United States Patent [19]
Sherman et al.

[11] Patent Number: 5,955,601
[45] Date of Patent: *Sep. 21, 1999

[54] LANTHANIDE CHELATE CONJUGATED OLIGONUCLEOTIDES

[75] Inventors: David Gordon Sherman, Sacramento; Charlene Elinor Bush, Davis; Laura Ann Beninsig, Elk Grove; Kurt Mathew VandenBrink, Sacramento, all of Calif.

[73] Assignee: E G & G Wallac, Turku, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/811,478

[22] Filed: Mar. 5, 1997

Related U.S. Application Data

[63] Continuation of application No. 08/273,287, Jul. 19, 1994, abandoned, which is a continuation of application No. 07/991,472, Dec. 19, 1992, abandoned, which is a continuation of application No. 07/655,707, Feb. 14, 1991, abandoned.

[51] Int. Cl.⁶ .................................................. C07H 21/04
[52] U.S. Cl. ...................... 536/26.6; 536/24.33; 536/121; 536/101
[58] Field of Search ..................... 536/26.6, 24.33, 536/121, 101; 435/6; 436/82, 172, 182

[56] References Cited

U.S. PATENT DOCUMENTS

| | | | |
|---|---|---|---|
| 4,058,732 | 11/1977 | Wieder | 250/461 B |
| 4,150,295 | 4/1979 | Wieder | 250/461 B |
| 4,563,419 | 1/1986 | Ranki et al. | 435/6 |
| 4,761,481 | 8/1988 | Hale et al. | 546/296 |
| 4,808,541 | 2/1989 | Mikola et al. | 436/501 |

FOREIGN PATENT DOCUMENTS

| | | |
|---|---|---|
| 0195413 | 9/1986 | European Pat. Off. |
| 0324323 | 7/1989 | European Pat. Off. |
| 88/02784 | 4/1988 | WIPO |
| 8802784 | 4/1988 | WIPO |
| 8904375 | 5/1989 | WIPO |
| 89/04826 | 6/1989 | WIPO |
| 8904826 | 6/1989 | WIPO |
| 90/00550 | 1/1990 | WIPO |
| 9000550 | 1/1990 | WIPO |
| 9000623 | 1/1990 | WIPO |

OTHER PUBLICATIONS

Ruth, et al., *Mol. Pharm.*, 20:45 (1981).
Brechbiel, et al., *Inorg. Chem.*, 25:2772 (1986).
Evangelista, et al., *Clin. Biochem.*, 21:173 (1988).
Langer, et al., *PNAS*, 78:6633 (1981).
Ranki, et al., *Gene*, 21:77 (1983).
Virtanen et al., *J. Clin. Microbiol.*, 20:1083 (1984).
Dahlen, et al., *Molecular and Cellular Probes*, 1:159 (1987).
Bresser et al., *DNA*, 2:243 (1983).
Oser, et al., *NAR*, 16:1181 (1988).
McCarthy et al., *Anal. Chem.*, 38:848 (1966).
Richardson, *Chem. Rev.*, 82:541 (1982).
Dahlen et al., *J. Clin. Microbiol.*, 26:2434–2436 (1988).
The 1988 Stratagene Catalog p. 39.
Sambrook et al. Molecular Cloning Cold Spring Harbor Laboratory Press, 1989, pp. 11.45–11.47.

*Primary Examiner*—Scott W. Houtteman
*Attorney, Agent, or Firm*—Adduci, Mastriani & Schaumberg, L.L.P.

[57] ABSTRACT

Rare earth chelate-conjugated oligonucleotides useful in nucleic acid hybridization assays and for generating chelate-labelled probes of any desired sequence are disclosed. The particular class of chelates utilized exhibit an unusually high efficiency of rare earth element capture, correlated with emission of a high level of signal in time-resolved fluorescence spectroscopy compared to other structurally related chelate compounds.

9 Claims, 3 Drawing Sheets

LANTHANIDE CHELATE CONJUGATED OLIGONUCLEOTIDES

This is a continuation of application Ser. No. 08/273,287, filed on Jul. 8, 1994, now abandoned, which is a continuation of 07/991,472, filed on Dec. 17, 1992, now abandoned, which is a continuation of 07/699,707, filed Feb. 14, 1991, now abandoned.

BACKGROUND OF THE INVENTION

The use of lanthanide chelates in nonisotopic labelling of biological macromolecules has attracted a great deal of interest in the field of diagnostics This technique takes advantage of the long lived fluorescence of lanthanide elements, compared to ordinary fluorescent backgrounds which otherwise tend to overwhelm genuine signal. The trivalent lanthanide ions $Eu^{+++}$, $Tb^{+++}$, and $Sm^{+++}$ all have fluorescent decay times on the order of milliseconds compared to nanosecond decay times for background fluorescence. By irradiating a sample at the appropriate wavelength and energy level, the fluorescence may be measured at a delayed point in time, after background fluorescence has already decayed, but while the lanthanide specimen is still emitting This technique is known as time-resolved, or time-gated fluorescence spectroscopy. For a general review of the principles of the technique, see U.S. Pat. Nos. 4,150,295 and 4,058,732, and Immunoflurescence and Related Staining Techniques, Knapp, et al. eds. (1978: Elsefier/North Holland Biomedical Press).

The fluorescent properties of lanthanide ions are generally enhanced when they are captured by a chelating agent. This is because hydration of the ion in aqueous solution drastically quenches the emitted energy. Chelation is also necessary to entrain the ions in proximity to the target which they are to detect.

Covalent coupling of chelating agents to proteins, such as antibodies with binding specificity to a targets and to nucleic acids, which will hybridize to specific complementary nucleic acid sequences, is known in the art. For example, WO 89/04375 (Musso) discloses labelling of DNA probes with EDTA, DTPA, and certain analogs thereof such as p-phenyl-EDTA, through a linker moiety having a terminal group with the formulae NH(C=S)NH, NH(C=O)NH, S(C=S)NH, etc. The probes are complexed with lanthanide ions and utilize a beta-diketone in micelles to increase sensitivity. Similarly, WO 88/02784 (Ylikoski) discloses multiple chelate labelled polymeric probes having chelate moities of the modified EDTA and DTPA type. WO 90/00550 (Kankare) discloses novel terpyridine derivatives which act as chelating agents for lanthanide ions and may have utility in labelling nucleic acid probes and proteins.

EP 0 324 323 (Hemmila) discloses chelates having a structure containing a heteroatom having a free electron pair selected from nitrogen, oxygen, phosphorus or sulfur, and being bonded so that the free electron pair is delocalized to a conjugated system of pi-bonds, useful in a homogeneous assay format WO 90/00623 (Kwiatkowski) discloses a multilabel nucleic acid probe system utilizing chelates having a bipyridine structure as a vehicle for multiple dicarboxylic acid groups.

The properties of various chelating agents differ with the type of biological macromolecule to which they are attached Of particular interest are the poly(arylpyridine) chelates which have large capacity to bind ions. The monosubstituted amino triazine ligand molecule having two diacid groups binds rare earth ions efficiently then attached to proteins such as antibodies, but has serious limitations in probe assays. In the context of protein labelling, the ligand combines at a number of sites which confer a conformational configuration conducive to ion binding. Naturally occuring carboxyl groups, such as the free carboxyl group of glutamic acid, also promote chelation. However, no such conformational interactions are possible with nucleic acids, which behave much like linear molecules. Thus, it is not readily apparent, nor can it be predicted, which chelate structures have especial efficacy in nucleic acid probe assays.

SUMMARY OF THE INVENTION

The present invention relates to novel lanthanide chelate-conjugated oligonucleotides utilized in hybridization assays for detection of nucleic acids present in a sample in small amounts, frequently in the presence of large quantities of non-homologous nucleic acids. Et is therefore an object of the present invention to obtain chelates capable of being conjugated covalently to oligonucleotides, which have extremely high level rare earth element capture efficiency, and corresponding high emission levels This is especially important in labelling of nucleic acids since indiscriminate multiple chelate labelling of nucleotide bases interferes with binding specificity.

Another object of the present invention, is to provide chelates which may be universally coupled to any nucleic acid sequence. The present chelates have an oligonucleotide tail of at least 4 nucleotides adapted for hybridization to a separate partially complementary nucleic acid strand. Upon hybridizing, a new strand complementary to that hybridized to the oligonucleotide tail may be synthesized by invitro enzyme-catalyzed polymerization utilizing the tail as a primer. Alternatively, a non-complementary strand can be incorporated into the chelated oligonucleotide by first hybridizing both the strand and the oligonucleotide to a bridging sequence, and then ligating. Alternatively, the oligonucleotide and a probe sequence can be blunt-end ligated with RNA ligase.

In accordance with the present invention, rare earth chelate-conjugated oligonuclectides have a rare earth chelate portion comprising one or a plurality of 2-alkoxy-4,6-di(N,N,N',N'-tetraalkyl)amino triazines in which one triazine carbon is covalently linked to a functionalized arylalkyl group selected from the group consisting of p-aminophenethoxy, p-isothiocyanophenethoxy, and p-thionylchlorophenethoxy, and the second and third triazine carbons are covalently coupled to an (aryl-dicarboxylpyridine)alkyl group; a linking group selected from the group consisting of an amide and a thiourea; and an oligonucleotide containing at least 4 consecutive underivatized deoxy- or ribo- nucleotides joined to the rare earth chelate through the linking group.

In another aspect of the present invention, the present chelate-conjugated oligonucleotides may be utilized in an assay for detecting a complementary nucleic acid in which the oligonucleotides are hybridized to a target nucleic acid sequence, followed by separating the hybridized nucleic acids, and detecting the extent of hybridization by measuring the signal generated by a signal means. The improvement in the assay comprises the oligonucleotide probe having at least 12 consecutive underivatized nucleotides having a nucleotide sequence complementary to a sample target sequence, which is linked covalently to a rare earth chelate comprising a tetra(arylpyridine) ligand having a tetramer of substituted arylpyridine diacid units attached covalently to a 2-alkoxy-4,6-diamino triazine radical.

Chelate-conjugated probes of any desired sequence can readily be constructed by hybridizing an oligonucleotide of at least 4 nucleotides which incorporates at the 3' or 5' terminus a rare earth chelate comprising a tetra(arylpyridine) having a tetramer of substituted arylpyridine diacid units covalently attached to a 2-alkoxy-4,6-diamino triazine radical, to a probe having a terminal sequence of at least 4 nucleotides complementary to the oligonucleotide, priming a polymerase-catalyzed extension reaction with the hybridized oligonucleotide, carrying out the extension reaction, separating the strands of the duplex, and isolating the chelate-tagged nucleic acid probe. Equivocally, the complementary strand may be removed by enzymatic digestion.

Alternatively, a chelate-tagged probe of any desired sequence can be constructed in a method comprising providing a bridging sequence complementary to an oligonucleotide of at least 4 consecutive underivatized nucleotides incorporating at the 3' or 5' terminus thereof, a rare earth chelate portion comprising a tetra(arylpyridine) ligands having a tetramer of substituted arylpyridine diacid units covalently attached to 2-alkoxy-4,6-diamino triazine radicals, which is also complementary to the terminus of a probe sequence of opposite 5'-3' polarity, hybridizing the bridging sequence to the oligonucleotide and the probe sequences and ligating the probe sequence to the oligonucleotide.

In a further embodiment of the present inventions a kit is provided for preparing chelate-tagged nucleic acid probes of any sequence incorporating a rare earth chelate-conjugated oligonucleotide comprising a first vessel containing an oligonucleotide of at least 4 nucleotides incorporating at the 3' or 5' terminus, a rare earth chelate comprising a tetra (arylpyridine) ligand having a tetramer of substituted arylpyridine diacid units covalently attached to a 2-alkoxy-4,6-diamino triazine radical, and a second vessel containing an enzyme selected from the group consisting of a polymerase and a ligase.

DETAILED DESCRIPTION OF THE PREFERRED EMBODIMENT

The general class of rare earth chelate molecules to which the nucleic acid conjugated chelates of the present invention belong is disclosed in Patent cooperation Treaty Application No. WO 89/04826 (Hale) and U.S. Pat. No. 4,761,481 (Hale). More specifically, the chelates having unusual efficacy in end-labelled nucleic acid probe assays comprise 2-alkoxy-4,6-di(N,N,N',N'-tetraalkyl) amino triazines of the structure

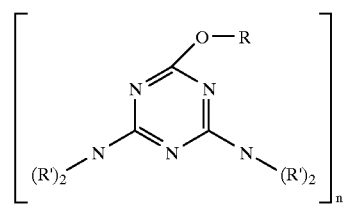

wherein R is a functionalized arylalkyl group selected from the group consisting of p-aminophenethoxy, p-isothiocyanophenethoxy, and p-thionylchlorophenethoxy; R' is an (aryl-dicarboxylpyridyl)alkyl group, and n is the number of triazines. The chelates are alternatively defined as tetra(arylpyridine) ligands comprising a tetramer of substituted arylpyridine diacid units covalently attached to a 2-alkoxy-4,6-diamino triazine radical.

A preferred substituted arylpyridine diacid unit is a (2,4-dialkoxy-5-(2,6-diacid-pyridyl)-phenyl)-alkyl group, and an even more preferred substituted arylpyridine diacid unit is the (2,4-dimethoxy-5-(2,6-dicarboxyl-pyridyl)-phenyl)-propyl group. Covalent coupling of the substituted arylpyridine diacid unit to the aminotriazine radical is conveniently obtained through a sulfonamido or similar group.

In synthesizing the chelates of the present invention, an aryl dicarboxylpyridinedialkoxyphenyl compound is converted to a functionalized aryl dicarboxylpyridinedialkyoxyphenyl derivative by chlorosulfonation, which is reacted with a functionalized triazine to yield the nitrophenethoxytetra (dialkoxyphenyldicarboxypyridine)triazine. All of the reactions and procedures are well-known in the literature.

The preferred chelate so synthesized is 2-(p-aminophenethoxy)-4,6-di (N,N,N',N'-tetra(3-propyl(2,4-(dimethoxy)-5-(2,6-di(carboxyl)-pyridyl sulfonamido)))-amino-triazine, hereafter referred to as Tetrakis. This compound, and others structurally related to it, have the advantages of being straightforward of synthesis, demonstrate high efficiency of rare earth element capture, low quenching, and relative ease of coupling to nucleic acid molecules.

Figure 1:
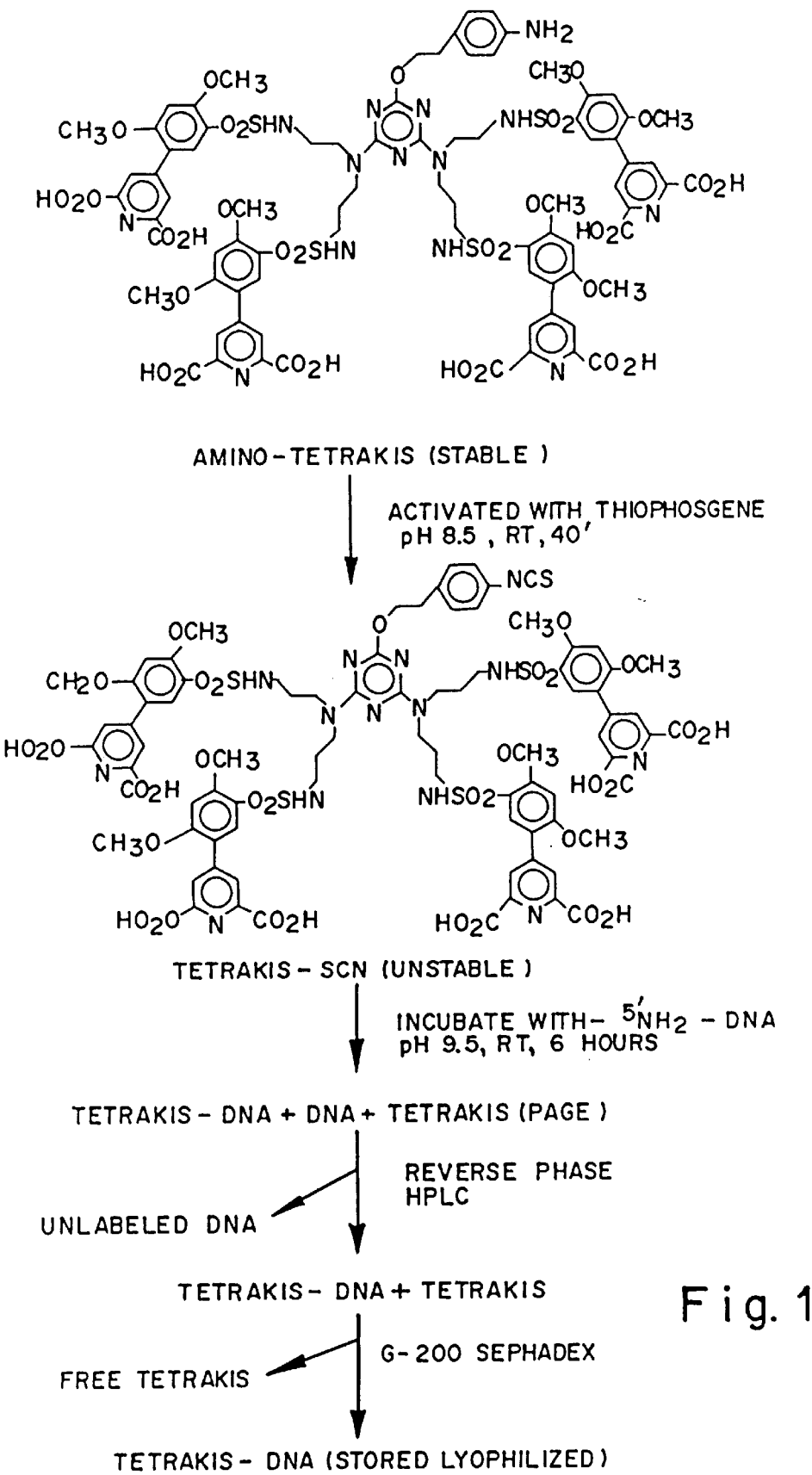
FIG. 1 shows a typical strategy for coupling of chelates to nucleic acids.

A typical strategy for coupling of chelates to nucleic acids is shown in FIG. 1 in which amino-tetrakis is activated with thiophosgene, followed by incubation with DNA, and purification of the reaction products by reverse phase HPLC and gel filtration through G-200 Sephadex. It is important that the intermediate isothiocyanate is not purified but reduced to dryness prior to coupling to nucleic acids. The DNA is also functionalized at either the 3' or 5' end to contain one or more amino groups linked directly to a phosphate group. Alternatively, an amino group attached to a nucleic acid base (such as the so-called "Ruth" base) may also be used to attach the chelate isothiocyanate. (See Ruth, et al., Mol. Pharm., 20:45 (1981).) An alternative to isothiocyanate coupling is thionyl chloride derivatization. Thus the linking group between the chelate and the nucleic acid may either be an amide or a thiourea. Other coupling technologies which may be utilized in attaching the chelates to oligonucleotide probes are described in Brechbiel, et al., Inorg. Chem., 25:2772 (1986), Evangelista, et al., Clin. Biochem., 21:173 (1988), and U.S. Pat. No. 4,808,541.

Figure 2A:
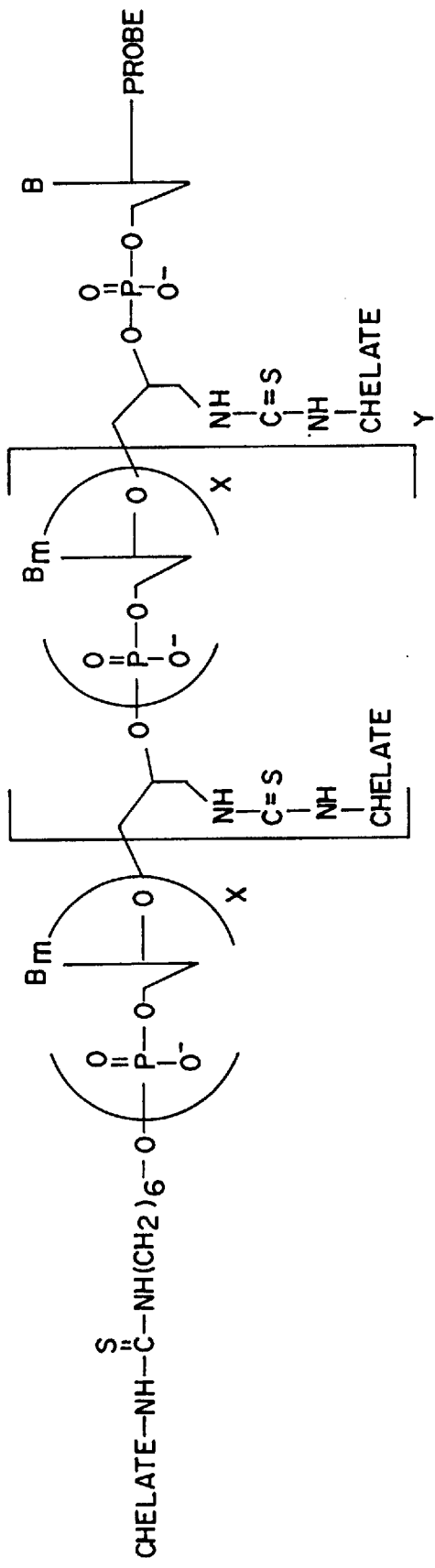
FIG. 2a shows a strategy of attaching multiple chelate molecules to either the 3' or 5' end of a nucleic acid probe to form a branched structure.
Figure 2B:
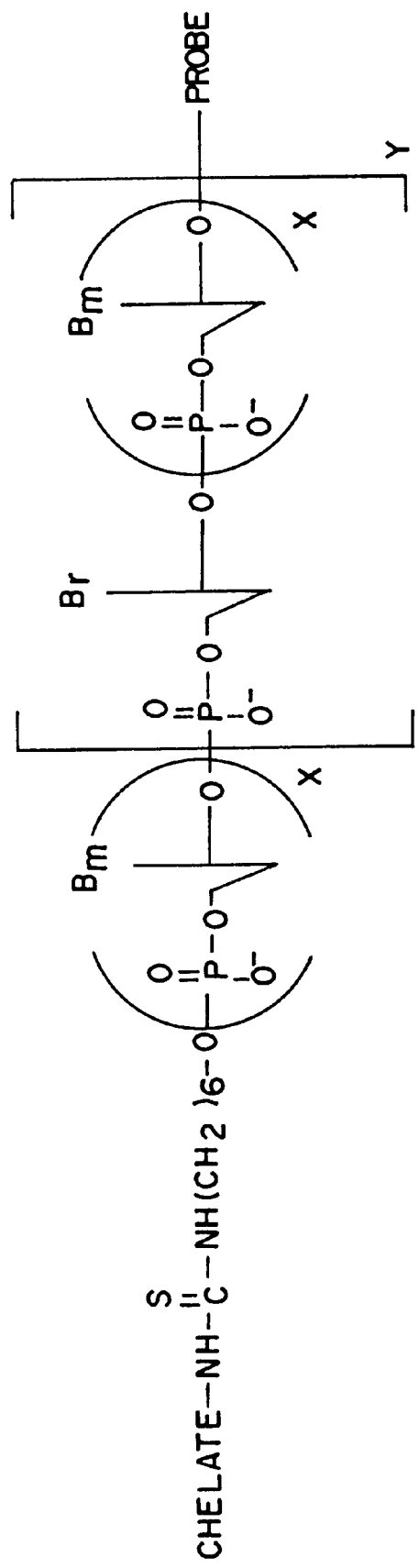
FIG. 2b shows a strategy of attaching multiple chelate molecules to either the 3' or 5' end of a nucleic acid probe to form a concatenated structure.

In order to enhance the sensitivity of assays utilizing chelate-conjugated probes, it is desirable to attach to the 3' or 5' end of nucleic acid probe sequences multiple chelate molecules either as a branching or concatenated structure. FIG. 2 illustrates these strategies schematically. In FIG. 2a a branched amino conjugate structure is repeated y times, with the terminal chelate positioned spacedly x bases from the first branching strucure. In FIG. 2b multiple labelling is effected by coupling through an amino derivatized uracil on alternating bases at either the 3' or 5' terminus of the probe. While any plurality of triazine conjugate moieties may theoretically be attached, the value for x is generally 4 or less, and that for y is 8 or less. Above this number of conjugates, a certain amount of steric hindrance to probe hybridization or interference with hybridization kinetics may be expected, although these parameters will be influenced by the size and base composition of the probe and target sequences.

In coupling the chelate molecules to an oligonucleotide, it is important that a "tail" of at least 4 underivatized nucleotides be preserved 3' or 5' of the chelate conjugated portion of the probe. Recognition of a complementary sequence by hybridization generally requires at least 4 bases. If n is the number of triazines in the chelate portion of a chelate-conjugated oligonucleotide, then the oligonucleotide, either a deoxy- or ribo-nucleotide, must contain at least 4 plus n nucleotides Preferably, the 4 nucleotides of the "tail" should be be consecutively underivatized to obtain maximum binding to a complementary sequence. The upper limit of nucleotides comprising the oligonucleotide probe may theoretically be on the order of kilobases. Functionally, however, a probe with minimally 12 bases substantially complementary to a target sequence is sufficient for adequate hybridizing discrimination in an assay, especially if the GC content is relatively high and the target sequence is highly conserved.

It is generally not intended that chelate-conjugated oligonucleotides with minimial length "tails" of about 4 nucleotides will be used as probes, but rather as tools in constructing probes of any given sequence, wherein the probe sequence is to be spliced onto the "tail" by blunt-end ligation utilizing RNA ligase. (See Sambrook, et al., Molecular Cloning: A Laboratory Manual, 2 ed., 1989.) Alternatively, splicing may be effected by T4 DNA ligase action on a single stranded nick in a duplex region spanning the end of the oligonucleotide and the probe According to this method, a bridging sequence is provided which is complementary to the tall sequence, and also complementary to the terminus of a probe sequence of opposite 5'-3' polarity. The bridging sequence is hybridized to the oligonucleotide tail and to the probe sequence under conventional hybridization conditions. Ligase is added to seal the blunt-end nick between the oligonucleotide tail and the probe, to create a continuously covalent molecule.

Alternatively, a chelate-conjugated tail oligonucleotide, of minimally 4 nucleotides, but preferably at least 12 nucleotides, is hybridized to a probe sequence complementary to the tail nucleotide wherein the terminal sequences are mutually complementary. The oligonucleotide tail is then used to prime a polymerase-catalyzed extension reaction along the probe sequence as template. The strands may then be separated, and the chelate-conjugated strand can readily be isolated, or the complementary strand may be digested enzymatically. The procedures for the polymerase extension reaction and strategies for strand separation and enzymatic digestion are conventional. See, for example, Sambrook, et al., Molecular Cloning: A Laboratory Notebook, 2 ed. New York:Cold Spring Harbor Laboratory, 1989, and Langer, et al., PNAS, 78:6633 (1981).

The oligonucleotide tail may also be selected as the sequence of nucleotides between the pair of staggered opposite stranded cuts of "sticky-ends" created by the activity of restriction endonucleases. Thus, the chelate-conjugated oligonucleotides of the present invention may be directly attached to restriction endonuclease digestion fragments of DNA from any source. The following are examples of such restriction enzymes and their corresponding recognition sequences: MboI(GATC), TaI(TCGA), Hind III (AAGCTT), EcoRI(GAATTC), and SacI(GAGCTC).

The chelate-conjugated oligonucleotide probes of the present invention can be utilized in any liquid or solid phase-based assay system capable of detecting duplex nucleic acids. Particularly advantageous are the "sandwich" type assays, preferably the bead-based sandwich assays. Examples of basic sandwich assay formats are described in Ranki, et al., Gene, 21:77 (1983), Virtanen, et al. J. Clin. Microbiol., 20:1083 (1984), and Dahlen, et al., Molecular and Cellular Probes, 1:159 (1987). Bead-based sandwich assays utilizing time-resolved fluorescence of rare earth chelates conjugated to nucleic acid probes are described in detail in WO89/04375 (Musso). Also advantageous in the practice of the present invention are solid phase-based assays such as Dot Blots which measure immobilized targets as described in Bresser, et al., DNA, 2:243 (1983), and Oser, et al., NAR, 16:1181 (1988).

The preferred assay format for detecting a complementary nucleic acid sequence contained in a sample comprises hybridizing a probe conjugated to a rare earth chelate with the sample under conditions favoring hybridization to a complementary target sequence contained within the sample, separating the hybridized nucleic acids, and then detecting the extent of hybridization by measuring the signal generated by the chelated rare earth metal ion bound to the chelate-conjugated probe. This is a more specific embodiment of the general assay format, equally applicable hereto, comprising hybridizing a probe containing a signal means to a target nucleic acid sequence contained in a sample, separating the hybridized nucleic acids, and detecting the extent of hybridization by measuring the signal generated by the signal means.

The assay of the present invention includes an improvement over the prior art in which an oligonucleotide probe is linked covalently to a rare earth chelate portion comprising tetra(arylpyridine) ligands comprising a tetramer of substituted arylpyridine diacid units covalently attached to 2-alkoxy-2,6-diamino triazine radicals. This is highly significant, and completely unexpected, in that the corresponding closely related analogue, identical Probe sequence coupled to a molecule of the following structure:

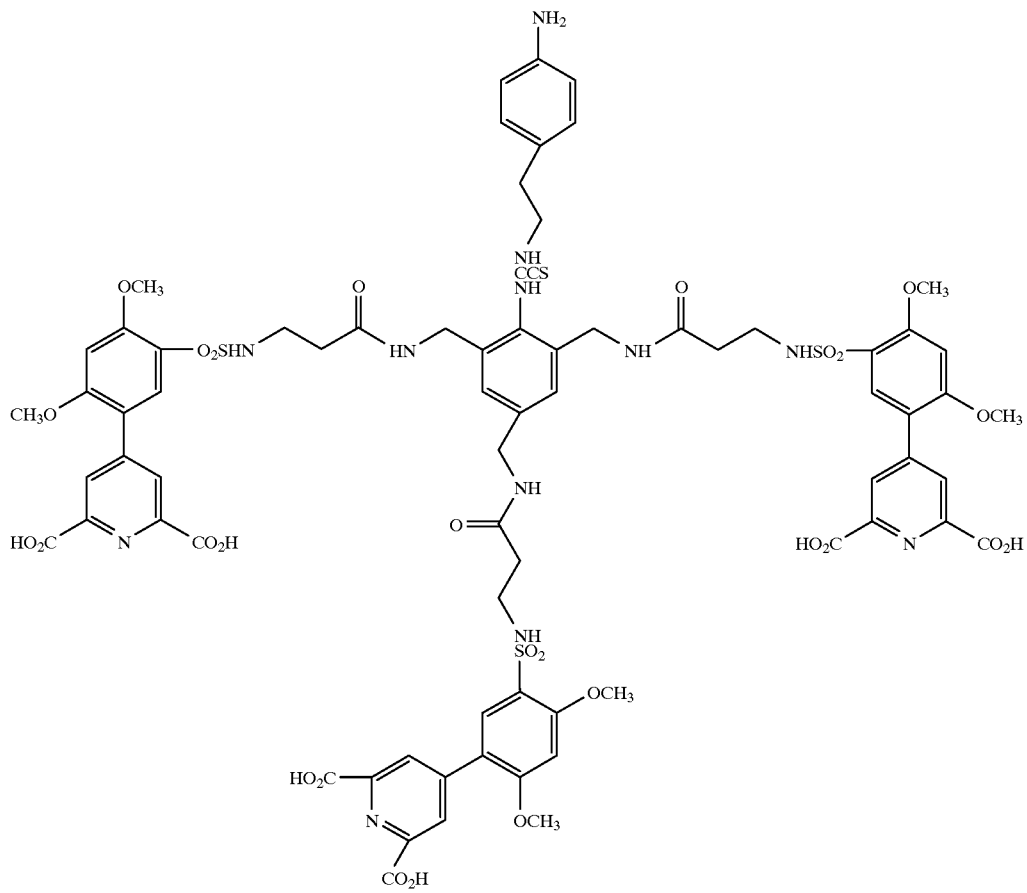

(hereinafter referred to as TRIS) shows extremely poor signal in the presence of $Tb^{+++}$, as does the nucleic acid-conjugated single corresponding dimethoxy-substituted arylpyridine dicarboxylic diacid compound (hereinafter referred to as PPTA). This is especially surprising since the optimum predicted signal is a TRIS configuration in view of the three faced coordination contact surfaces of the $Eu^{+++}$ and $Tb^{+++}$ atoms.

In another aspect of the present invention, a kit is provided which contains a first vessel containing an oligonucleotide of at least 4 nucleotides incorporating at the 3' or 5' terminus a rare earth chelate of the type described hereinabove; and a second vessel containing an enzyme such as a polymerase for chain extension, or a DNA ligase to seal abuttments of nucleic acid segments utilizing a bridging sequence or an RNA ligase to that blunt-end joinder. The solutions of such vessel ingredients are preferably sealed hermetically, and frozen until desired use. Additional advantages of the present invention are to be understood from the following Examples.

EXAMPLE 1

PPTA labelled DNA was prepared according to the procedures described in U.S. Pat. No. 4,761,481 (Hale et al.). 50 ul of $HSO_3Cl$ was placed in a 1.5 ml Eppendorf snap cap vial and placed into 0.0 degrees C. water bath. To this solution was added 5.0 mg of PPTA in 5 approximately 1.0 mg quantities over a period of 5 minutes. The solution was stirred continuously during the PPTA addition, and the temperature maintained at 0.0 degrees C. The solution was allowed to stir for about 15 minutes before adding the solution very slowly to about 200 ul of ice. The resulting pale yellow solid was removed by centrifugation and washed twice with cold water. The PPTA thionyl chloride was dissolved in 100 ul, 0.2 M sodium borate, pH 9.5. To this solution of a 35 base oligomer, having the sequence TTTTT, AAC GGG TAC TTA TAC ACA ACT CAA AAA GTG, functionalized on the 5' end with 6-amino hexylphosphate. The 35 base oligomer was prepared using an Applied Biosystems Inc. synthesizer. The reaction mixture was allowed to stir at room temperature for 6 hours. The reaction mix was poured over a column of G-200 Sephadex, and eluted with water. The first peak was collected and lyophilized. The resultant white powder was evaluated by UV scan showing maxima at 260 and 316 nm respectively. The unlabelled DNA absorbed at 260 nm only. The 14% denaturing PAGE gel showed a band migrating slightly slower than the starting DNA, and was positive to a terbium stain.

EXAMPLE 2

Functionalized amino-TRIS was prepared by dissolving 7.0 mg amino-TRIS in 100 ul water with LiOH (10 mg). To this solution was added 100 ul of 0.5 M sodium carbonate and 200 ul water. 5 ul of thiophosgene was added in 200 ul chloroform to the chelate solution in about 75 ul increments, and vortexed for about 1 minute between additions. The solution was allowed to set for about 10 minutes with intermittent stirring. The solution was then dried under reduced pressure to yield a cream colored solids which is used without further purification. TRIS-DNA was prepared from the above TRIS isothiocyanate upon redissolution in water. 57 nmoles of the 35 base oligonucleotide specified in Example 1 above, functionalized on the 5 ' end with 6-aminohexyl phosphate was dissolved in 0.1 M sodium borate pH 9.5. The chelate solution and oligomer solution were combined and allowed to react for 12 hours with stirring. The reaction mixture was purified by a two step process of 1) reverse phase HPLC using a gradient of 50 mM triethyl ammonium acetate and acetonitrile, and 2) G-200 gel filtration, with water as the eluant. The purified labelled oligomer was characterized upon a 14% denaturing PAGE gel.

EXAMPLE 3

TETRAKIS-DNA was prepared utilizing precisely the same procedures as for the preparation of TRIS-DNA set forth in Example 2 hereinabove. Spectrophotometric and PAGE analysis gave confirmation of the formation of the chelate-DNA conjugate.

EXAMPLE 4

Comparison of the PPTA-DNA

4(2,4-dimethoxyphenyl)-2,6-di(N,N,N', N'tetracarboxyethyl)-methylaminopyridine, TRIS-DNA, and TETRAKIS-DNA chelate-conjugated nucleic acids was carried out utilizing a bead based sandwich hybridization protocols as follows: In a well of a Deltar plate (Pandex 22-010-2) 10 ul of a bead suspension of polystyrene beads (5 mg/ml) to which was bound a target complementary sequence to the probe sequence set forth in Example 1 hereinabove, was incubated with 25 ul 2×hyridization solution consisting of 10×SSC (1.5 M Sodium chloride, 0.15 M Sodium citrate), 50 mM MOPS ((3-(n-Morpholino)propane-sulfonic acid)). 100 fmoles of detection labelled oligonucleotide was added and incubated at 50 degrees C. for 1 hour.

The beads were separated from the medium by vacuuming, and washed several times by addition of 0.1× SSC buffer (0.015 M Sodium chlorides 0.0015 M Sodium citrate). A resuspension solution of 1×SSC, 0.2 M Magnesium chloride was added followed by a $Tb^{30\ ++}$, EDTA (Ethylenediaminetetraacetic acid) solution. The solution was incubated for 10 minutes. Samples were read in a fluorescence time-resolved instrument at the exciting and emission wave lengths specified in McCarthy, et al., Anal. Chem., 38:848 (1966), and Richardson, Chem. Rev., 82:541 (1982).

The results are given in Table 1A below for the comparison of PPTA, TRIS, and the claimed TETRAKIS compounds. The first column shows the value of the chelate-conjugated probe in a bead-based sandwich hybridization reaction of the sequence of Example 1 with its complementary target. The control values in the second column are for the binding of probe to beads omitting a target sequence, and the values in the third column are the S:N ratios or signal to noise ratio.

It is apparent from the data that the TETRAKIS compounds show an approximately 10 fold increase in signal (photons) compared to the closely related TRIS compound chelate. Comparatively, the difference in TETRAKIS and TRIS structure is negligible, even though it could be expected that the TRIS chelates would engage all of the molecular interaction surfaces presented by the rare earth ions. This data correlates well with the results of Table 1B for direct capture of rare earth ion.

TABLE 1A

SANDWICH HYBRIDIZATION (includes target)
50 femtomoles target used

|  | POSITIVE | NEGATIVE | S:N |
|---|---|---|---|
| Tetrakis | 40468 | 1654 | 24:1 |
| Tris | 4920 | 1690 | 3:1 |
| PPTA | 1114 | 975 | 1:1 |

TABLE 1B

DIRECT CAPTURE
10 femtomoles chelate labeled probe

|  | POSITIVE | NEGATIVE | S:N | COUNTS/FM |
|---|---|---|---|---|
| Tetrakis | 8240 | 55 | 150:1 | 820 |
| Tris | 952 | 55 | 17:1 | 90 |
| PPTA | 806 | 55 | 15:1 | 75 |

Table 2 shows that the level of sensitivity of this assay is on the order of $1 \times 10^{-17}$ mol, and compares well to chemiluminescent technologies for acridinium esters and luminol enhancers.

TABLE 2

| Substrate | Detection mode | Detection limit for label mol | Detection limit in probe assay, mol |
|---|---|---|---|
| MUBP* | fluorometer | $8 \times 10^{-20}$ | $1 \times 10^{-19}$ |
| Isoluminol | luminometer | $1 \times 10^{-18}$ | $1 \times 10^{-13}$ |
| Acridinium Ester | luminometer | $2 \times 10^{-16}$ | $2 \times 10^{-17}$ |
| Luminol and Enhancer | luminometer | $6 \times 10^{-17}$ | $6 \times 10^{-17}$ |
| $Tb^{+3}$/Tetrakis | Time-resolved fluorometer | $1 \times 10^{-17}$ | $5 \times 10^{-17}$ |
| D-luciferin-o-phosphate | luminometer | $6 \times 10^{-20}$ | $1 \times 10^{-19}$ |
| 1,2-dioxetane | luminometer film | $1 \times 10^{-20}$ | $1 \times 10^{-19}$ |

*Methylumbilliferone

Table 3 shows that a double chelate (concatenate wherein y=2) produces an additively enhanced signal compared to the single conjugate, in an assay of similar format to that given above. The data show that detection in the 0.1 fm ($10^{-16}$ mol) range is possible with multiple labels.

TABLE 3

Single vs. Multiple Labelled Chelate

| Chelate conc | Single | Multiple |
|---|---|---|
| 2 fm | 2614 | 5676 |
| 1 fm | 1486 | 3076 |
| 0.5 fm | 596 | 1538 |
| 0.2 fm | 287 | 798 |
| 0.1 fm | — | 407 |

Data from chelate single labelled probe 88–300 and multiple labelled probe 2120.

Data obtained through direct capture assay.

Multiple-chelate has approximately 2 chelates per probe sequence. The number of chelates was determined spectrophotometrically.

What is claimed is:

1. Rare earth chelate-conjugated oligonucleotides comprising a fluorescent rare earth chelate portion comprising one or a plurality of 2-alkoxy-4,6-di(N,N,N',N'-tetraalkyl) amino triazines of the structure

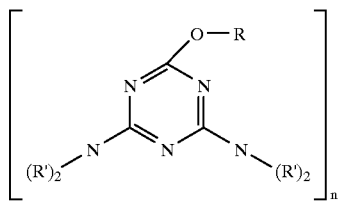

wherein R is a functionalized arylalkyl group selected from the group consisting of p-aminophenethoxy, p-isothiocyanophenethoxy, and p-thionylchlorophenethoxy, R' is a 2,6-di(carboxyl)-4-aryl pyridyl group, and n is the number of said triazines, a linking group; and an oligonucleotide containing at least 4 plus n deoxy- or ribo-nucleotides joined covalently to said rare earth chelate through said linking group.

2. Rare earth chelate-conjugated oligonucleotides comprising tetra(arylpyridine) ligands, each said ligand comprising a tetramer of 2,6-di(carboxyl)-4-aryl pyridyl moiety units covalently attached to a 2-alkoxy-4,6-diamino triazine radical, an oligonucleotide having at least 4 consecutive underivatized nucleotides; and a linking group conjugating said oligonucleotide to each said 2-alkoxy-4,6-diamino triazine radical.

3. In an assay for detecting a complementary nucleic acid sequence comprising hybridizing a probe containing a signal means to a target nucleic acid sequence contained in a sample, separating the hybridized nucleic acids, and detecting the extent of hybridization by measuring the signal generated by said signal molecule, the improvement comprising, providing as the signal means, the rare earth chelate conjugated oligonucleotide of claim 1 wherein the oligonucleotide has at least 12 consecutively underivatized nucleotides having a nucleotide sequence complementary to a nucleic acid sequence contained in a sample.

4. In an improved assay for detecting a complementary nucleic acid sequence comprising hybridizing a probe containing a signal means to a target nucleic acid sequence contained in a sample, separating the hybridized nucleic acids, and detecting the extent of hybridization by measuring the signal generated by said signal molecule, the improvement comprising incubating the rare earth chelate conjugated oligonucleotide of claim 1 wherein the oligonucleotide portion has at least 12 consecutively underivatized nucleotides having a nucleotide sequence complementary to a nucleic acid sequence contained in a sample, separating said rare earth conjugated oligonucleotide probe and target nucleic acid sequence so hybridized from the sample, incubating the hybridized rare earth conjugated oligonucleotide probe and target nucleic acid sequence in the presence of a rare earth element to effect chelation; and measuring the extent of chelation by first exciting the rare earth element with radiation of excitation wavelength, and then measuring the emission fluorescence by time-resolved fluorescence spectroscopy.

5. Chelate-tagged nucleic acid probes of any sequence incorporating the rare earth chelate-conjugated oligonucleotide of claim 1 wherein the oligonucleotide portion has at least 12 nucleotides, said chelate-tagged nucleic acid probe made by the process comprising hybridizing the oligonucleotide to a sequence complementary to a probe and having a terminal sequence complementary to the oligonucleotide, priming a polymerase-catalyzed extension reaction with the oligonucleotide sequence so hybridized, carrying out the extension reaction, separating the strands of the duplex so formed; and isolating the chelate-tagged nucleic acid probe.

6. Chelate-tagged nucleic acid probes of any sequence incorporating a rare earth chelate-conjugated oligonucleotide constructed by a method comprising providing a bridging sequence complementary to an oligonucleotide of at least 4 consecutive underivatized nucleotides incorporating at the 3' or 5' terminus thereof a rare earth chelate portion comprising one or a plurality of tetra(arylpyridine) ligands, each said ligand having a tetramer of 2,6-di(carboxyl)-4-aryl pyridyl moiety units covalently attached to 2-alkoxy-4,6-diamino triazine radicals, wherein said bridging sequence is also complementary to the terminus of a probe sequence of opposite 5'–3' polarity, hybridizing the bridging sequence to the oligonucleotide and the probe sequence; and ligating the probe sequence to the oligonucleotide.

7. Chelate-tagged nucleic acid probes of any sequence incorporating a rare earth chelate-conjugated oligonucleotide constructed by a method comprising ligating with RNA ligase any desired probe sequence to an oligonucleotide tail of at least 4 consecutive underivatized nucleotides conjugated to a rare earth chelate portion comprising one or a plurality of tetra(arylpyridine) ligands, each said ligand having a tetramer of 2,6-di(carboxyl)-4aryl pyridyl moiety units covalently attached to 2-alkoxy-4,6-diamino triazine radicals.

8. The chelate-tagged probes of claims 7 or 8 therein said oligonucleotide has the sequence of nucleotides between the pair of staggered opposite stranded cuts created by the activity of restriction endonucleases.

9. A kit for preparing chelate-tagged nucleic acid probes of any sequence incorporating the rare earth chelate-conjugated oligonucleotide of claim 1 comprising a first vessel containing the rare earth chelate-conjugated oligonucleotide; and a second vessel containing an enzyme selected from the group consisting of a polyermase and a ligase.

* * * * *